(12) United States Patent
Johnson et al.

(10) Patent No.: US 6,521,638 B1
(45) Date of Patent: Feb. 18, 2003

(54) 2,3-DIHYDRO-1H-ISOINDOLE DERIVATIVES USEFUL AS MODULATORS OF DOPAMINE $D_3$ RECEPTORS (ANTIPSYCHOTIC AGENTS)

(75) Inventors: Christopher Norbert Johnson, Saffron Walden (GB); Geoffrey Stemp, Bishop's Stortford (GB)

(73) Assignee: SmithKline Beecham p.l.c., Brentford (DE)

( * ) Notice: Subject to any disclaimer, the term of this patent is extended or adjusted under 35 U.S.C. 154(b) by 0 days.

(21) Appl. No.: 09/806,894

(22) PCT Filed: Oct. 6, 1999

(86) PCT No.: PCT/EP99/07762

§ 371 (c)(1),
(2), (4) Date: Jun. 8, 2001

(87) PCT Pub. No.: WO00/21950

PCT Pub. Date: Apr. 20, 2000

(30) Foreign Application Priority Data

Oct. 8, 1998 (GB) .............................................. 9821978

(51) Int. Cl.$^7$ ................ A61K 31/4709; A61K 31/4439; A61K 31/4035; C07D 401/12; C07D 403/12; C07D 209/44

(52) U.S. Cl. ........................ 514/314; 514/300; 514/339; 514/406; 514/415; 514/416; 546/113; 546/16.9; 546/227.1; 548/364.7; 548/482

(58) Field of Search .................................. 546/113, 169, 546/227.1; 548/364.7, 482; 514/300, 314, 339, 406, 415, 416

(56) References Cited

FOREIGN PATENT DOCUMENTS

| EP | 0 431 580 | 6/1991 |
|----|-----------|--------|
| WO | WO 94 21628 | 9/1994 |
| WO | WO 97 43262 | 11/1997 |
| WO | WO 98 06699 | 2/1998 |
| WO | WO 98 50364 | 11/1998 |

*Primary Examiner*—Evelyn Mei Huang
(74) *Attorney, Agent, or Firm*—Nora Stein-Fernandez; Stephen A. Venetianer; Charles M. Kinzig

(57) ABSTRACT

Compounds of formula (I) wherein $R^1$, $R^2$, A, q are as defined herein, and salts thereof, have affinity for dopamine receptors, in particular the D3 receptor, and thus have potential in the treatment of conditions wherein modulation of the D3 receptor is beneficial, e.g. as antipsychotic agents.

Formula (I)

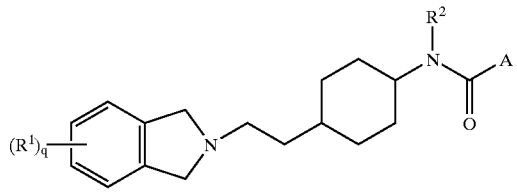

6 Claims, No Drawings

2,3-DIHYDRO-1H-ISOINDOLE DERIVATIVES USEFUL AS MODULATORS OF DOPAMINE D₃ RECEPTORS (ANTIPSYCHOTIC AGENTS)

This application is the 371 of PCT/EP99/07762, filed on Oct. 6,1999.

The present invention relates to novel 2,3-dihydro-1H-isoindole derivatives, processes for their preparation, pharmaceutical compositions containing them and their use in therapy, as modulators of dopamine $D_3$ receptors, in particular as antipsychotic agents.

U.S. Pat. No. 5,294,621 describes tetrahydropyridine derivatives of the formula:

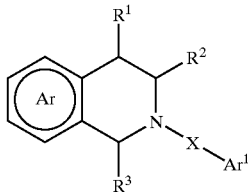

wherein

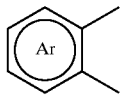

is an optionally substituted thienyl or optionally substituted phenyl ring; $R^1$, $R^2$ and R3 are each inter alia hydrogen; X is inter alia $(CH_2)mNR^7CO$; m is 2–4; and $Ar^1$ is an optionally substituted heterocyclic ring or an optionally substituted phenyl ring. The compounds are said to be useful as antiarrhythmic agents.

EPA 431,580 describes compounds of formula

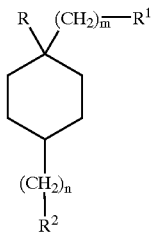

wherein R is $OR^3$, $NR^4R^5$, or $N(OR^4)R^5$, $R^4$ and $R^5$ are inter alia hydrogen, lower alkyl, aroyl or heteroaroyl; m is zero, 1 or 2; $R^1$ is hydrogen, aryl or various heteroaryl groups; n is zero or 1–4; and $R^2$ is:

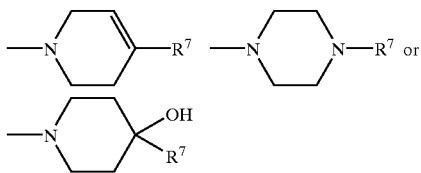

The compounds are said to be dopaminergic agents useful as antipsychotics, antihypertensives and also of use in the treatment of hyperprolactinaemia-related conditions and several central nervous system disorders.

WO 95/10513 describes benzothiophene derivatives and related compounds as estrogen agonists.

WO 97/43262 and WO 98/06699 describe tetrahydroisoquinoline derivatives as having affinity for the dopamine $D_3$ receptor.

We have now found a class of 2,3-dihydro-1H-isoindole derivatives which have affinity for dopamine receptors, in particular the $D_3$ receptor, and thus potential in the treatment of conditions wherein modulation of the $D_3$ receptor is beneficial, eg as antipsychotic agents.

In a first aspect the present invention provides compounds of formula (I):

Formula (I)

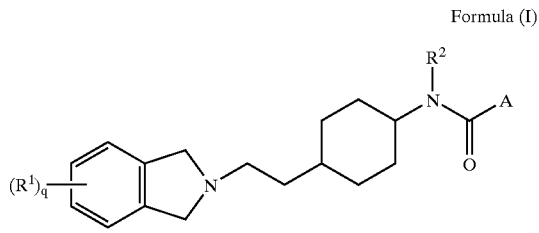

wherein:

$R^1$ represents a substituent selected from: a hydrogen or halogen atom; a hydroxy, cyano, nitro, trifluoromethyl, trifluoromethoxy, trifluoromethanesulfonyloxy, pentafluoroethyl, $C_{1-4}$alkyl, $C_{1-4}$alkoxy, aryl$C_{1-4}$alkoxy, $C_{1-4}$alkylthio, $C_{1-4}$alkoxy$C_{1-4}$alkyl, $C_{3-6}$cycloalkyl$C_{1-4}$alkoxy, $C_{1-4}$alkanoyl, $C_{1-4}$alkoxycarbonyl, $C_{1-4}$alkylsulfonyl, $C_{1-4}$alkylsulfonyloxy, $C_{1-4}$alkylsulfonyl$C_{1-4}$alkyl, arylsulfonyl, arylsulfonyloxy, arylsulfonyl$C_{1-4}$alkyl, $C_{1-4}$alkylsulfonamido, $C_{1-4}$alkylamido, $C_{1-4}$alkylsulfonamido$C_{1-4}$alkyl, $C_{1-4}$alkylamido$C_{1-4}$alkyl, arylsulfonamido, arylcarboxamido, arylsulfonamido$C_{1-4}$alkyl, arylcarboxamido$C_{1-4}$alkyl, aroyl, aroyl$C_{1-4}$alkyl, or aryl$C_{1-4}$alkanoyl group; a group $R^3OCO(CH_2)_p$, $R^3CON(R^4)(CH_2)_p$, $R^3R^4NCO(CH_2)_p$ or $R^3R^4NSO_2(CH_2)_p$ where each of $R^3$ and $R^4$ independently represents a hydrogen atom or a $C_{1-4}$alkyl group or $R^3R^4$ forms part of a $C_{3-6}$azacyloalkane or $C_{3-6}$(2-oxo)azacycloalkane ring and p represents zero or an integer from 1 to 4; or a group $Ar^3$—Z, wherein Ar3 represents an optionally substituted phenyl ring or an optionally substituted 5- or 6-membered aromatic heterocyclic ring and Z represents a bond, O, S, or $CH_2$;

$R^2$ represents a hydrogen atom or a $C_{1-4}$alkyl group;

q is 1 or 2;

A represents a group of the formula (a), (b), (c) or (d):

(a) 

(b) 

(c) 

(d) 

Ar represents an optionally substituted phenyl ring or an optionally substituted 5- or 6- membered aromatic heterocyclic ring; or an optionally substituted bicyclic ring system;

$Ar^1$ and $Ar^2$ each independently represent an optionally substituted phenyl ring or an optionally substituted 5- or 6-membered aromatic heterocyclic ring; and Y represents a bond, —NHCO—, —CONH—, —CH₂—, or —(CH2)$_m$Y$^1$(CH2)$_n$—, wherein Y$^1$ represents O, S, SO$_2$, or CO and m and n each represent zero or 1 such that the sum of m+n is zero or 1; providing that when A represents a group of formula (a), any substituent present in Ar ortho to the carboxamide moiety is necessarily a hydrogen or a methoxy group;

r and s independently represent an integer from zero to 3 such that the sum of r and s is equal to an integer from 1 to 4;

V represents a bond, O or S;

and salts thereof.

In the compounds of formula (I) above an alkyl group or moiety may be straight or branched. Alkyl groups which may be employed include methyl, ethyl, n-propyl, n-butyl, n-pentyl, n-hexyl and any branched isomers thereof such as isopropyl, t-butyl, sec-butyl, and the like.

When $R^1$ represents an aryl$C_{1-4}$alkoxy, arylsulfonyl, arylsulfonyloxy, arylsulfonyl$C_{1-4}$alkyl, arylsulfonamido, arylcarboxamido, arylsulfonamido$C_{1-4}$alkyl, arylcarboxamido$C_{1-4}$alkyl, aroyl, aroyl$C_{1-4}$alkyl, or aryl$C_{1-4}$alkanoyl group, the aryl moiety may be selected from an optionally substituted phenyl ring or an optionally substituted 5- or 6-membered heterocyclic ring. In the group $R^1$ an aryl moiety may be optionally substituted by one or more substituents selected from hydrogen, halogen, amino, cyano, $C_{1-4}$alkyl, $C_{1-4}$alkylamino, $C_{1-4}$dialkylamino, $C_{1-4}$alkylamido, $C_{1-4}$alkanoyl, or $R^5R^6NCO$ where each of $R^5$ and $R^6$ independently represents a hydrogen atom or $C_{1-4}$alkyl group.

A halogen atom present in the compounds of formula (I) may be fluorine, chlorine, bromine or iodine.

When q is 2, the substituents $R^1$ may be the same or different.

An optionally substituted 5- or 6-membered heterocyclic aromatic ring, as defined for any of the groups Ar, $Ar^1$, $Ar^2$ or $Ar^3$ may contain from 1 to 4 heteroatoms selected from O, N or S. When the ring contains 2–4 heteroatoms, one is preferably selected from O, N and S and the remaining heteroatoms are preferably N. Examples of 5 and 6-membered heterocyclic groups include furyl, thienyl, pyrrolyl, oxazolyl, thiazolyl, imidazolyl, oxadiazolyl, thiadiazolyl, pyridyl, triazolyl, triazinyl, pyridazyl, pyrimidinyl, isothiazolyl, isoxazolyl, pyrazinyl and pyrazolyl.

Examples of bicyclic, for example bicyclic aromatic or heteroaromatic, ring systems for Ar include naphthyl, indazolyl, indolyl, benzofuranyl, benzothienyl, benzothiazolyl, benzimidazolyl, benzoxazolyl, benzisoxazolyl, benzisothiazolyl, quinolinyl, quinoxolinyl, quinazolinyl, cinnolinyl, isoquinolinyl, pyrazolo[1,5-a]pyrimidyl, pyrrolo[3,2-b]pyridyl, pyrrolo[3,2-c]pyridyl, thieno[3,2-b]thiophenyl, 1,2-dihydro-2-oxo-quinolinyl, 3,4-dihydro-2-oxo-4H-benzoxazinyl, 1,2-dihydro-2-oxo-3H-indolyl.

The rings Ar, $Ar^1$, or $Ar^2$ may each independently be optionally substituted by one or more substituents selected from: a hydrogen or halogen atom, or a hydroxy, oxo, cyano, nitro, trifluoromethyl, $C_{1-4}$alkyl, $C_{1-4}$alkoxy, $C_{1-4}$alkylenedioxy, $C_{1-4}$alkanoyl, $C_{1-4}$alkylsulfonyl, $C_{1-4}$alkylsulfinyl, $C_{1-4}$alkylthio, $R^7SO_2N(R^8)$—, $R^7R^8NSO_2$—, $R^7R^8N$—, $R^7R^8NCO$—, or $R^7CON(R^8)$— group wherein each of $R^7$ and $R^8$ independently represents a hydrogen atom or a $C_{1-4}$ alkyl group, or $R^7R^8$ together form a $C_{3-6}$ alkylene chain.

Alternatively, Ar and $Ar^2$ may be optionally substituted by one or more 5- or 6-membered heterocyclic rings, as defined above, optionally substituted by a $C_{1-2}$ alkyl or $R^7R^8N$— group; wherein $R^7$ and $R^8$ are as defined above.

In the rings Ar and $Ar^2$ substituents positioned ortho to one another may be linked to form a 5- or 6-membered ring.

It will be appreciated that for use in medicine the salts of formula (I) should be physiologically acceptable. Suitable physiologically acceptable salts will be apparent to those skilled in the art and include for example acid addition salts formed with inorganic acids eg. hydrochloric, hydrobromic, sulfuric, nitric or phosphoric acid; and organic acids eg. succinic, maleic, acetic, fumaric, citric, tartaric, benzoic, p-toluenesulfonic, methanesulfonic or naphthalenesulfonic acid. Other non-physiologically acceptable salts eg. oxalates, may be used, for example in the isolation of compounds of formula (I) and are included within the scope of this invention. Also included within the scope of the invention are solvates and hydrates of compounds of formula (I).

Certain of the compounds of formula (I) may form acid addition salts with one or more equivalents of the acid. The present invention includes within its scope all possible stoichiometric and non-stoichiometric forms.

The compounds of formula (I) can exist in the form of cis- and trans-isomers with respect to the configuration at the cyclohexyl ring. When A represents a group (c) the compounds may also exist as geometric isomers around the double bond. The present invention includes within its scope all such isomers, including mixtures. Preferably the compounds of the invention are in the trans configuration with respect to the cyclohexyl ring. For compounds of formula (I) where A represents a group (c), trans geometry of the double bond is preferred.

In compounds of formula (I), it is preferred that $R^1$ represents a substituent selected from: a halogen atom, methyl, cyano, trifluoromethyl, pentafluoroethyl, methylsulfonyloxy or trifluoromethoxy group. Preferably q is 1. $R^2$ is preferably a hydrogen atom.

The group A is preferably a group of formula (a), (b) or (c). With regard to (a), preferred examples of Ar include optionally substituted indolyl, pyrazolo[1,5-a]pyrimidyl, cinnolinyl, quinolinyl, benzo[b]furanyl or pyrrolopyridyl. With regard to (c), preferred examples are optionally substituted phenyl groups.

It is also preferred that the rings Ar, $Ar^1$, or $Ar^2$ are each independently optionally substituted by one or more substituents selected from: a hydrogen or halogen atom, cyano, methoxy, methylenedioxy, acetyl, acetylamino, methylsulfonyl, methylsulfonyloxy, methylaminosulfonyl, methylsulfonylamino, or methylaminocarbonyl group.

Certain of the substituted heteroaromatic ring systems included in compounds of formula (I) may exist in one or more tautomeric forms. The present invention includes within its scope all such tautomeric forms, including mixtures.

Particular compounds according to the invention include those specifically exemplified and named hereinafter. These compounds may be in the form of their free base or physiologically acceptable salts thereof, particularly the monohydrochloride or monomesylate salts.

The present invention also provides a process for preparing compounds of formula (I) which process comprises:

(a) reacting a compound of formula (II):

Formula (II)

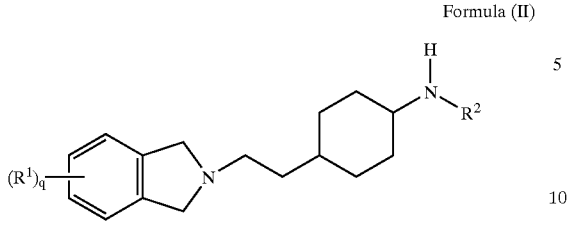

wherein $R^1$, $R^2$ and q are as hereinbefore defined, with a compound of formula (III):

A—COX  Formula (III)

wherein A is as hereinbefore defined and X is a halogen atom or the residue of an activated ester;

(b) to prepare a compound of formula (I) by reacting a compound of formula (II) with a compound A—Br, or A—I, or A—OSO$_2$CF$_3$ in the presence of carbon monoxide and a catalyst such as trans-bis-triphenylphosphinepalladium(II)bromide;

(c) to prepare a compound of formula (I) wherein $R^1$ is Ar$^3$—Z and Z is a bond, reacting a compound of formula (IV):

Formula (IV)

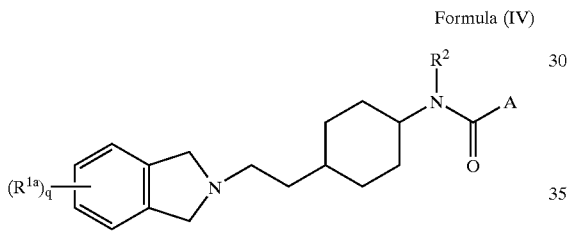

wherein $R^2$ and A are as hereinbefore defined and one $R^{1a}$ represents a group W wherein W is a halogen atom or a trifluoromethylsulfonyloxy group, or W is a group M selected from a boron derivative e.g. a boronic acid function B(OH)$_2$ or a metal function such as trialkylstannyl e.g. SnBu$_3$, zinc halide or magnesium halide, and when q is 2 the other $R^{1a}$ is $R^1$; with a compound Ar$^3$—W$^1$, wherein W$^1$ is a halogen atom or a trifluoromethylsulfonyloxy group when W is a group M or W$^1$ is a group M when W is a halogen atom or a trifluoromethylsulfonyloxy group;

(d) to prepare a compound of formula (I) wherein $R^1$ is Ar$^3$—Z and Z is O or S, reacting a compound of formula (V):

Formula (V)

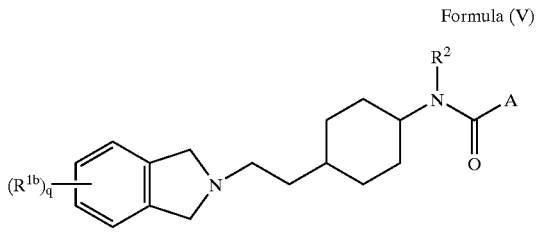

wherein $R^2$ and A are as hereinbefore defined and one $R^{1b}$ represents a group ZH and when q is 2 the other $R^{1b}$ represents $R^1$; with a reagent serving to introduce the group Ar$^3$;

(e) to prepare a compound of formula (I) where Y is a bond, reaction of a compound of formula (VI):

Formula (VI)

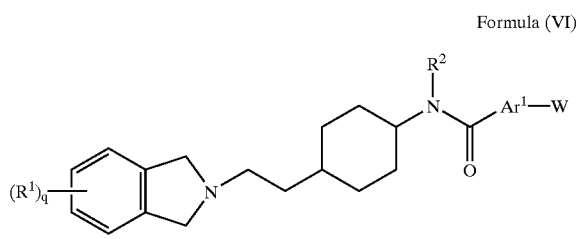

wherein $R^1$, $R^2$, Ar$^1$, W and q are as hereinbefore defined, with a compound Ar$^2$—W$^1$, wherein W$^1$ is a halogen atom or a trifluoromethylsulfonyloxy group when W is a group M, or W$^1$ is a group M when W is a halogen atom or a trifluoromethylsulfonyloxy group.

(f) interconversion of one compound of formula (I) to a different compound of formula (I) e.g. (i) alkylation of a compound (I) wherein $R^2$ represents hydrogen, (ii) conversion of one $R^1$ from alkoxy (e.g.methoxy) to hydroxy, or (iii) conversion of $R^1$ from hydroxy to sulfonyloxy, eg alkylsulfonyloxy or trifluoromethanesulfonyloxy; (iv) conversion of a compound wherein Y represents S to a compound wherein Y is SO$_2$ or (v) conversion of Y from CO to CH$_2$;

(g) separation of cis- and trans-isomers of compounds of formula (I) by conventional methods, e.g. chromatography or crystallisation; and optionally thereafter forming a salt of formula (I).

Process (a) may be effected using conventional methods for the formation of an amide bond. When X is the residue of an activated ester this may be formed with e.g. a carbodiimide such as 1-ethyl-3-(3-dimethylaminopropyl)carbodiimide. The reaction may be carried out in a solvent such as dichloromethane.

Reaction of a compound of formula (IV) with Ar$^3$W$^1$, according to process (c) or a compound of formula (VI) with Ar$^2$—W$^1$ according to process (e) may be effected in the presence of a transition metal eg palladium catalyst such as bis-triphenylphosphinepalladium dichloride or tetrakis-triphenylphosphinepalladium (0). When M represents a boronic acid function such as B(OH)$_2$ the reaction may be carried out under basic conditions, for example using aqueous sodium carbonate in a suitable solvent such as dioxane. When M is trialkylstannyl the reaction may be carried out in an inert solvent, such as xylene or dioxane optionally in the presence of LiCl. When M is a zinc or magnesium halide the reaction may be effected in an aprotic solvent such as tetrahydrofuran. The substituent W is preferably a halogen atom such as bromine, or a sulfonyloxy group such as trifluoromethylsulfonyloxy; and W$^1$ is preferably a goup M, such as trialkylstannyl or B(OH)$_2$.

In process (d) the reagent serving to introduce the group Ar$^3$ is preferably a compound of formula Ar$^3$—Hal, wherein Hal is a halogen atom. The reaction may be effected in the presence of a base, such as potassium carbonate, in a solvent such as dimethylformamide.

Interconversion reactions according to process (f) may be effected using methods well known in the art.

Compounds of formula (II) may be prepared by conversion of a compound of formula (VII), wherein $R^1$ and q are as hereinbefore defined, Formula (VII)

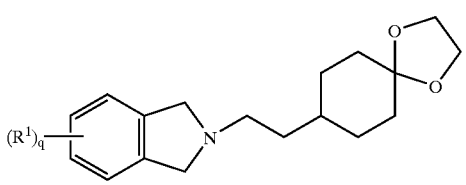

into a corresponding ketone, followed by reductive amination. This may be effected by methods well known in the art for (i) conversion of a ketal to a ketone in the presence of aqueous acid; followed by (ii) reductive amination of the ketone with $R^2NH_2$ or ammonium acetate in the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as methanol, ethanol or dichloroethane.

A compound of formula (VII) may itself be prepared by reacting a compound of formula (VIII):

Formula (VIII)

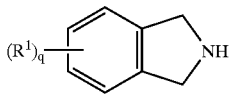

wherein $R^1$ and q are as hereinbefore defined; with a compound of formula (IX):

Formula (IX)

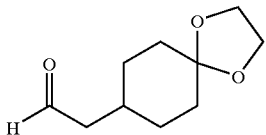

in the presence of a reducing agent. Suitable reducing agents which may be employed include sodium borohydride, cyanoborohydride or triacetoxyborohydride under acidic conditions, or catalytic hydrogenation. The reaction may conveniently be effected in a solvent such as ethanol or dichloroethane.

The individual cis- and trans-isomers of a compound of formula (II) may be prepared starting from cis- or trans-4-amino-cyclohexaneacetic acid (T. P. Johnson, et al., J. Med. Chem., 1997, (20), 279–290) followed by functional group interchange and/or protection using methods well known in the art, to give the individual cis- or trans-isomers of a compound of formula (X):

Formula (X)

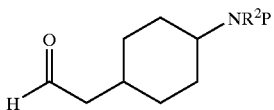

wherein $R^2$ is as hereinbefore defined, and P is a protecting group, for example trifluoroacetyl or tert-butoxycarbonyl. Subsequent reaction of a compound of formula (X) with a compound of formula (VIII) in the presence of a reducing agent as described above followed by deprotection using standard methodology gives the individual isomers of a compound of formula (II) wherein $R^2$ is as hereinbefore defined.

Compounds of formula (m) are known or may be prepared using standard procedures.

Compounds of formula (IV), (V) or (VI) may be prepared by processes analogous to (a), (b), (c) and (d) described above. Compounds $Ar^2W^1$, $Ar^3W^1$ and $Ar^3Hal$ are commercially available or may be prepared by standard methods. Compounds of formula (VIII) are known in the literature or may be prepared by known methods. The compound of formula (IX) is likewise known in the literature.

Compounds of formula (I) have been found to exhibit affinity for dopamine receptors, in particular the $D_3$ receptor, and are expected to be useful in the treatment of disease states which require modulation of such receptors, such as psychotic conditions. Compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. Without wishing to be bound by theory, it has been suggested that blockade of the recently characterised dopamine $D_3$ receptor may give rise to beneficial antipsychotic activity without significant eps. (see for example Sokoloff et al, Nature, 1990; 347: 146–151; and Schwartz et al, Clinical Neuropharmacology, Vol 16, No. 4, 295–314, 1993). Preferred compounds of the present invention are therefore those which have higher affinity for dopamine $D_3$ than dopamine $D_2$ receptors (such affinity can be measured using standard methodology for example using cloned dopamine receptors). Said compounds may advantageously be used as selective modulators of $D_3$ receptors.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (eg see Schwartz et al., Brain Res. Reviews, 1998, 26, 236–242). From the localisation of D3 receptors, it could also be envisaged that the compounds could also have utility for the treatment of substance abuse where it has been suggested that D3 receptors are involved (eg see Levant, 1997, Pharmacol. Rev., 49, 231–252). Examples of such substance abuse include alcohol, cocaine and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

In a further aspect therefore the present invention provides a method of treating conditions which require modulation of dopamine $D_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine $D_3$ receptors, for example psychoses such as schizophrenia.

In a further aspect therefore the present invention provides a method of treating conditions which require modulation of dopamine $D_3$ receptors, for example psychoses such as schizophrenia, which comprises administering to a subject in need thereof an effective amount of a compound of formula (I) or a physiologically acceptable salt thereof.

The invention also provides the use of a compound of formula (I) or a physiologically acceptable salt thereof in the manufacture of a medicament for the treatment of conditions which require modulation of dopamine $D_3$ receptors, for example psychoses such as schizophrenia.

A preferred use for $D_3$ antagonists according to the present invention is in the treatment of psychoses such as schizophrenia.

For use in medicine, the compounds of the present invention are usually administered as a standard pharmaceutical composition. The present invention therefore provides in a further aspect pharmaceutical compositions comprising a novel compound of formula (I) or a physiologically acceptable salt thereof and a physiologically acceptable carrier.

The compounds of formula (I) may be administered by any convenient method, for example by oral, parenteral, buccal, sublingual, nasal, rectal or transdermal administration and the pharmaceutical compositions adapted accordingly.

The compounds of formula (I) and their physiologically acceptable salts which are active when given orally can be formulated as liquids or solids, for example syrups, suspensions or emulsions, tablets, capsules and lozenges.

A liquid formulation will generally consist of a suspension or solution of the compound or physiologically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or physiologically acceptable salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

Preferably the composition is in unit dose form such as a tablet, capsule or ampoule.

Each dosage unit for oral administration contains preferably from 1 to 250 mg (and for parenteral administration contains preferably from 0.1 to 25 mg) of a compound of the formula (I) or a physiologically acceptable salt thereof calculated as the free base.

The physiologically acceptable compounds of the invention will normally be administered in a daily dosage regimen (for an adult patient) of, for example, an oral dose of between 1 mg and 500 mg, preferably between 10 mg and 400 mg, e.g. between 10 and 250 mg or an intravenous, subcutaneous, or intramuscular dose of between 0.1 mg and 100 mg, preferably between 0.1 mg and 50 mg, e.g. between 1 and 25 mg of the compound of the formula (I) or a physiologically acceptable salt thereof calculated as the free base, the compound being administered 1 to 4 times per day. Suitably the compounds will be administered for a period of continuous therapy, for example for a week or more.

Biological Test Methods

The ability of the compounds to bind selectively to human $D_3$ dopamine receptors can be demonstrated by measuring their binding to cloned receptors. The inhibition constants ($K_i$) of test compounds for displacement of $[^{125}I]$ iodosulpride binding to human $D_3$ dopamine receptors expressed in CHO cells were determined as follows. The cell lines were shown to be free from bacterial, fungal and mycoplasmal contaminants, and stocks of each were stored frozen in liquid nitrogen. Cultures were grown as monolayers or in suspension in standard cell culture media. Cells were recovered by scraping (from monolayers) or by centrifugation (from suspension cultures), and were washed two or three times by suspension in phosphate buffered saline followed by collection by centrifugation. Cell pellets were stored frozen at $-40°$ C. Crude cell membranes were prepared by homogenisation followed by high-speed centrifugation, and characterisation of cloned receptors achieved by radioligand binding.

Preparation of CHO Cell Membranes

Cell pellets were gently thawed at room temperature, and resuspended in about 20 volumes of ice-cold 50 mM Tris salts (pH 7.4 @ 37° C.), 20 mM EDTA, 0.2 M sucrose. The suspension was homogenised using an Ultra-Turrax at full speed for 15 sec. The homogenate was centrifuged at 18,000 r.p.m for 20 min at 4° C. in a Sorvall RC5C centrifuge. The membrane pellet was resuspended in ice-cold 50 mM Tris salts (pH 7.4 @ 37° C.), using an Ultra-Turrax, and recentrifuged at 18,000 r.p.m for 15 min at 4° C. in a Sorvall RC5C. The membranes were washed two more times with ice-cold 50 mM Tris salts (pH 7.4 @ 37° C.). The final pellet was resuspended in 50 mM Tris salts (pH 7.4 @ 37° C.), and the protein content determined using bovine serum albumin as a standard (Bradford, M. M. (1976) Anal. Biochem. 72, 248–254).

Binding Experiments on Cloned Dopamine Receptors

Crude cell membranes were incubated with 0.1 nM [$^{125}$I] iodosulpride (~2000 Ci/mmol; Amersham, U. K.), and the test compound in a buffer containing 50 mM Tris salts (pH 7.4 @ 37° C.), 120 mM NaCl, 5 mM KCl, 2 mM CaCl$_2$, 1 mM MgCl2, 0.1% (w/v) bovine serum albumin, in a total volume of 1 ml for 30 min at 37° C. Following incubation, samples were filtered using a Brandel Cell Harvester, and washed three times with ice-cold 50 mM Tris salts (pH 7.4 @ 37° C.), 120 mM NaCl, 5 mM KCl, 2 mM CaCl$_2$, 1 mM MgCl$_2$. The radioactivity on the filters was measured using a Cobra gamma counter (Canberra Packard). Non-specific binding was defined as the radioligand binding remaining after incubation in the presence of 100 µM iodosulpride. For competition curves, 14 concentrations (half-log dilutions) of competing cold drug were used. Competition curves were analysed simultaneously whenever possible using non-linear least-squares fitting procedures, capable of fitting one, two or three site models.

Compounds of Examples tested according to this method had pKi values in the range 7.0–8.5 at the human cloned dopamine D$_3$ receptor.

Functional Activity at Cloned Dopamine Receptors

The functional activity of compounds at human D2 and human D3 receptors (ie agonism or antagonism) may be determined using a Cytosensor Microphysiometer (McConnell HM et al Science 1992 257 1906–1912) In Microphysiometer experiments, cells (hD2_CHO or hD3_CHO) were seeded into 12 mm Transwell inserts (Costar) at 300000 cells/cup in foetal calf serum (FCS)-containing medium. The cells were incubated for 6 h at 37° C. in 5%CO$_2$, before changing to FCS-free medium. After a further 16–18 h, cups were loaded into the sensor chambers of the Cytosensor Microphysiometer (Molecular Devices) and the chambers perfused with running medium (bicarbonate-free Dulbecco's modified Eagles medium containing 2 mM glutamine and 44 mM NaCl) at a flow rate of 100 ul/min. Each pump cycle lasted 90s. The pump was on for the first 60s and the acidification rate determined between 68 and 88s, using the Cytosoft programme. Test compounds were diluted in running medium. In experiments to determine agonist activity, cells were exposed (4.5 min for hD2, 7.5 min for hD3) to increasing concentrations of putative agonist at half hour intervals. Seven concentrations of the putative agonist were used. Peak acidification rate to each putative agonist concentration was determined and concentration-response curves fitted using Robofit [Tilford, N. S., Bowen, W. P. & Baxter, G. S. Br. J. Pharmacol. (1995). In press]. In experiments to determine antagonist potency, cells were treated at 30 min intervals with five pulses of a submaximal concentration of quinpirole (100 nM for hD2 cells, 30 nM for hD3 cells), before exposure to the lowest concentration of putative antagonist. At the end of the next 30 min interval, cells were pulsed again with quinpirole (in the continued presence of the antagonist) before exposure to the next highest antagonist concentration. In all, five concentrations of antagonist were used in each experiment. Peak acidification rate to each agonist concentration was determined and concentration-inhibition curves fitted using Robofit.

Pharmaceutical Formulations

The following represent typical pharmaceutical formulations according to the present invention, which may be prepared using standard methods.

| IV Infusion | |
| --- | --- |
| Compound of formula (I) | 1–40 mg |
| Buffer | to pH ca 7 |
| Solvent/complexing agent | to 100 ml |
| Bolus Injection | |
| Compound of formula (I) | 1–40 mg |
| Buffer | to pH ca 7 |
| Co-Solvent | to 5 ml |

Buffer: Suitable buffers include citrate, phosphate, sodium hydroxide/hydrochloric acid.
Solvent: Typically water but may also include cyclodextrins (1–100 mg) and co-solvents such as propylene glycol, polyethylene glycol and alcohol.

| Tablet | |
| --- | --- |
| Compound | 1–40 mg |
| Diluent/Filler* | 50–250 mg |
| Binder | 5–25 mg |
| Disentegrant* | 5–50 mg |
| Lubricant | 1–5 mg |
| Cyclodextrin | 1–100 mg |

*may also include cyclodextrins

Diluent: e.g. Microcrystalline cellulose, lactose, starch
Binder: e.g. Polyvinylpyrrolidone, hydroxypropymethylcellulose
Disintegrant: e.g. Sodium starch glycollate, crospovidone
Lubricant: e.g. Magnesium stearate, sodium stearyl fumarate.

| Oral Suspension | |
| --- | --- |
| Compound | 1–40 mg |
| Suspending Agent | 0.1–10 mg |
| Diluent | 20–60 mg |
| Preservative | 0.01–1.0 mg |
| Buffer | to pH ca 5–8 |
| Co-solvent | 0–40 mg |
| Flavour | 0.01–1.0 mg |
| Colourant | 0.001–0.1 mg |

Suspending agent: e.g. Xanthan gum, microcrystalline cellulose
Diluent: e.g. sorbitol solution, typically water
Preservative: e.g. sodium benzoate
Buffer: e.g. citrate
Co-solvent: e.g. alcohol, propylene glycol, polyethylene glycol, cyclodextrin The invention is further illustrated by the following non-limiting examples:

Description 1 trans-2-(1(4(N- tert-Butyloxycarbonyl)amino) cyclohexyl)acetic acid, methyl ester A mixture of trans-(4-amino)cyclohexylacetic acid hydrogen sulfate (T. P. Johnston et al; J. Med Chem., 1977, 20 (2), 279–290), (27.0 g, 106 mmol), conc. H$_2$SO$_4$ (3 ml), and methanol (300 ml) was stirred at reflux for 5 h. Resulting solution was filtered and the filtrate evaporated in vacuo to give a brown oil (36 g). A mixture of this material, triethylamine (36 ml; 26.1 g, 259 mmol), dichloromethane (600 ml) and di-t-butyl dicarbonate (25.5 g, 117 mmol) was stirred at 20° C. for 18 h. Resulting solution was partitioned between saturated aqueous NaHCO$_3$ (500 ml) and dichloromethane (3×200 ml), and the combined extracts were dried (Na$_2$SO$_4$) and evaporated in vacuo to give the title compound (24.6 g, 86%) as a colourless solid.

$^1$H NMR (CDCl$_3$) δ: 1.08 (4H, m), 1.43 (9H, s), 1.76 (3H, m), 2.00 (2H, m), 2.20 (2H, d, J=7 Hz), 3.37 (1H, m), 3.66 (3H, s), 4.39 (1H, br s).

Description 2 trans -2-(1-(4-(N-tert-Butyloxycarbonyl)amino) cyclohexyl)acetaldehyde

To a stirred solution of trans-2-(1-(4-(N-tert-butyloxycarbonyl)amino)cyclohexyl)acetic acid, methyl ester (46.0 g, 170 mmol) in dry toluene (920 ml) at −78° C. under argon was added a solution of di-isobutylaluminium hydride (1M; 285 ml; 285 mmol), dropwise over 0.5 h. Resulting solution was stirred for a further 0.3 h and quenched with a mixture of methanol (28 ml) in toluene (50 ml) and then poured into saturated aqueous potassium sodium tartrate (1.2 L). The resultant mixture was extracted with ether (4×1 L). The combined organic extracts were dried (Na$_2$SO$_4$) and evaporated in vacuo to give a waxy solid which was purified using silica gel, eluting with 10–50% ethyl acetate/hexane to give the title compound (21.77 g, 53%) as a colourless solid.

$^1$H NMR (CDCl$_3$) δ: 1.12 (4H, m), 1.44 (9H, s), 1.78 (3H, m), 2.00 (2H, m), 2.33 (2H, dd, J=7,2 Hz), 3.37 (1H, m), 4.40 (1H, m), 9.75 (1H, m).

Description 3 trans-2-(2-(1-(4-(N-tert-Butyloxycarbonyl)amino) cyclohexyl)ethyl)-2,3-dihydro-1H-isoindole A mixture of trans-2-(1-(4-(N-tert-butyloxycarbonyl) amino)cyclohexyl)acetaldehyde (6.8 g, 25.2 mmol), 2,3-dihydro-1H-isoindole (3.00 g, 25.2 mmol) (J. Borrstein, J. E. Shields and A. P. Boisselle; Org. Syn. Coll. Vol. V.; Baumgarten, H. E., Ed; Wiley: New York, 1973; pp 406–408), sodium triacetoxyborohydride (8.0 g, 37.8 mmol) in 1,2-dichloroethane (100 ml) was stirred at 20° C. for 16 h. Resulting solution was partitioned between saturated NaHCO$_3$ (500 ml) and dichloromethane (200 ml), and the combined extracts were saturated NaHCO$_3$), dried (Na$_2$SO$_4$) and evaporated. The residue was chromatographed on silica gel eluting with ethyl acetate hexane mixtures to afford the title compound (6.5 g, 75%) as a pale pink solid.

$^1$H NMR (CDCl$_3$) δ: 1.00–1.11 (4H, m), 1.30–1.60 (3H, m), 1.44 (9H, s), 1.80–182 (2H, m), 1.98–2.04 (2H, m), 2.72 (2H, t, J=8 Hz), 3.37 (1H, m), 3.90 (4H, s), 4.35 (1H, s) and 7.18 (4H, s).

Description 4 trans-2-(2-(1-(4-Amino)cyclohexyl)ethyl)-2,3-dihydro-1H-isoindole

A mixture of trans-2-(2-(1-(4-(N-tert-butyloxycarbonyl) amino)cyclohexyl)ethyl)-2,3-dihydro-1H-isoindole (6.4 g, 18.6 mmol), trifluoroacetic acid (10 ml) and dichloromethane (100 ml) was stirred at ca 40° C. for 45 min. Resulting solution was evaporated in vacuo and the residue partitioned between water (200 ml) and ethyl acetate (100 ml). The aqueous layer was washed with ethyl acetate (100 ml) then basified to pH 14 with 2M NaOH, and extracted with dichloromethane (3×300 ml). The combined organic extracts, dried (Na$_2$SO$_4$) and evaporated in vacuo to give the title compound (4.01 g, 90%) as a pale brown solid.

Mass spectrum (API$^+$): Found 245 (MH$^+$). C$_{16}$H$_{24}$N$_2$ requires 244.

$^1$H NMR (CDCl$_3$) δ: 0.93–1.20 (4H, m), 1.20–1.40 (1H, m), 1.50–1.60 (4H, m), 1.70–1.90 (4H, m), 2.60 (1H, m), 2.73 (2H, t, J=8 Hz), 3.90 (4H, s) and 7.18 (4H, s).

Description 5

2-(tert-Butyloxycarbonyl)-5-hydroxy-2,3-dihydro-1H-isoindole

5-Methoxy-2,3-dihydro-1H-isoindole (28.7 g) was dissolved in 48% hydrobromic acid (620 ml) and the mixture heated under reflux for 2 h, then cooled and evaporated to give 5-hydroxy-2,3-dihydro-1H-isoindole hydrobromide (29.5 g) as a brown solid. To the above hydrobromide salt (29.5 g) in tetrahydrofuran (215 ml) and water (215 ml) at 0° C. was added triethylamine (48 ml) followed by di-tert-butyl dicarbonate (33 g). The reaction was stirred for 18 h, then worked up as for Description 1 above and chromatographed on silica gel, to give the title compound (13.2 g, 29%) as a brown solid.

Mass spectrum (API$^+$): Found 136 [M-Boc]H$^+$. C$_{13}$H$_{17}$NO$_3$ requires 235.

Description 6

2-(tert-Butyloxycarbonyl)-5-cyano-2,3-dihydro-1H-isoindole

Trifluoromethanesulfonic anhydride (9.6 ml) was added to a solution of 2-(tert-butyloxycarbonyl)-5-hydroxy-2,3-dihydro-1H-isoindole (12.2 g) and triethylamine (8.7 ml) at −20° C. under argon. The reaction was stirred overnight at room temperature, then the crude product isolated by extraction and chromatographed to give 2-(tert-butyloxycarbonyl)-5-trifluoromethanesulfonyloxy-2,3-dihydro-1H-isoindole (12.7 g), which was dissolved in DMF (180 ml). To this solution was added zinc cyanide (3.7 g) and tetrakis-triphenylphosphine palladium (0) (3.7 g) and the mixture was heated at 100° C. for 4 h. Work-up and chromatography on silica gel gave the title compound as a solid (7.6 g, 83%).

Mass spectrum (API$^+$): Found 145 [M-Boc]H$^+$. C$_{14}$H$_{16}$N$_2$O$_2$ requires 244.

Description 7

5-Cyano-2,3-dihydro-1H-isoindole

A mixture of 2-(tert-butyloxycarbonyl)-5-cyano-2,3-dihydro-1H-isoindole (7.6 g) and trifluoroacetic acid (20 ml) in dichloromethane (200 ml) was heated at 40° C. for 0.5 h, then cooled and evaporated in vacuo and the residue partitioned between dichloromethane and 2M sodium hydroxide. The aqueous phase was re-extracted with dichloromethane and the combined organics dried and evaporated to give the title compound as a pink solid (4.24 g, 94%).

Mass spectrum (API$^+$): Found 145 MH$^+$. C$_9$H$_8$N$_2$ requires 144.

Description 8

2-(tert-Butyloxycarbonyl)-5-methanesulfonyloxy-2,3-dihydro-1H-isoindole

The title compound (2.3 g, 69%) was prepared from 2-(tert-butyloxycarbonyl)-5-hydroxy-2,3-dihydro-1H- isoindole (2.5 g) and methanesulfonyl chloride (1.7 ml) using the method of Description 6.

Mass spectrum (API$^+$): Found 214 [M-Boc]H$^+$. $C_{14}H_{19}NO_5S$ requires 313.

Description 9

5-Methanesulfonyloxy-2,3-dihydro-1H-isoindole

The title compound (1.4 g, 90%) was prepared from 2-(tert-butyloxycarbonyl)-5-methanesulfonyloxy-2,3-dihydro-1H-isoindole using the method of Description 7.

Mass spectrum (API$^+$): Found 214 MH$^+$. $C_9H_{11}NO_3S$ requires 213.

EXAMPLE 1 trans-2-(2-(1-(4-(4-quinolinyl)carboxamido) cyclohexyl)ethyl)-2,3-dihydro-1H-isoindole A mixture of trans-2-(2-(1-(4-amino) cyclohexyl)ethyl)-2,3-dihydro-1H-isoindole (0.1 g: 0.35 mmol), 4-quinolinecarboxylic acid (0.061 g; 0.35 mmol), 1-ethyl-3-(3-dimethylaminopropyl)carbodiimide hydrochloride (0.067 g; 0.35 mmol), 1-hydroxybenzotriazole (catalytic amount) and dichloromethane (4 ml) was shaken for 16 h. Saturated aqueous sodium bicarbonate (4 ml) was added and the mixture shaken for 0.25 h. Chromatography of the organic layer on silica eluting with 30–100% ethyl acetate in hexane and 0–10% methanol in ethyl acetate gradient elution gave the title compound as a solid.

Mass spectrum (API$^+$): Found 400 (MH$^+$). $C_{26}H_{29}N_3O$ requires 399.

$^1$H NMR (CDCl,) δ: 1.10–1.50 (5H, m), 1.50–1.60 (2H, mn), 1.89–1.93 (2H, mn), 2.18–2.22 (2H, mn), 2.73–2.79 (2H, m), 3.92 (4H, s), 4.05 (1H, m), 5.94 (1H, J=8 Hz), 7.20 (4H, s), 7.39 (1H, d, J=4 Hz), 7.60 (1H, dt, J=8, 1 Hz), 7.75 (1H, dt, J=5, 1 Hz), 8.14 (1H, d, J=8 Hz), 8.16 (1H, d, J=8 Hz) and 8.91 (1H, d, J=4 Hz).

The Following Compounds Were Prepared According to the Procedure of Example 1

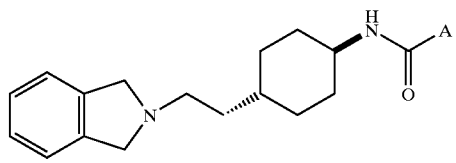

| Example | A | Characterising Data<br>Mass spectrum (API$^+$)<br>$^1$HNMR δ(CDCl$_3$ or d$_6$-DMSO) |
|---|---|---|
| 2 | ![structure with SO2Me] SO$_2$Me | MH$^+$453.$C_{26}H_{32}N_2O_3S$ requires 452.<br>1.10–1.28(4H, m), 1.40–1.50(1H, m), 1.50–1.55 (2H, m), 1.85–1.90(2H, m), 2.04–2.09(2H, m), 2.75(2H, t, J=8 Hz), 3.07(3H, s), 3.86(1H, m), 3.91(4H, s), 5.50(1H, d, J=8.Hz), 6.48(1H, d, J=16Hz), 7.19(4H, s), 7.58(1H, t, J=8 Hz), 7.62(1H, d, J=16Hz), 7.72(1H, d, J=8Hz), 7.89(1H, d, J=8Hz) and 8.09 (1H, s). |
| 3 | ![structure with F] F | MH$^+$393. $C_{25}H_{29}N_2FO$ requires 392.<br>1.10–1.20(4h, M), 1.40–1.50(1H, m), 1.50–1.55 (2H, m), 1.85–1.90(2H, m), 2.04–2.08(2H, m), 2.75(2H, t, J=8 Hz), 3.86(1H, m), 3.92(4H, s), 5.39(1H, d, J=8Hz), 6.26(1H, d, J=16Hz), 7.05 (2H, t, J=8Hz), 7.20(4H, s), 7.45–7.49(2H, m) and7.57(1H, d, J=16Hz). |
| 4 | ![methylphenyl-pyridyl structure] | MH$^+$426. $C_{28}H_{31}N_3O$ requires 425.<br>1.16–1.30(4H, m), 1.40–1.50(1H, m), 1.50–1.60 (2H, m), 1.88–1.91(2H, m), 2.12–2.16(2H, m), 2.76(2H, t, J=8Hz), 3.92(4H, s), 3.98(1H, m), 5.94(1H, d, J=8Hz), 7.19(4H, s), 7.40(1H, m), 7.65(2H, m), 7.85–7.90(3H, m), 8.60–8.65(1H, m) and 8.85–8.88(1H, m). |
| 5 | ![ethylnaphthyl structure] | MH$^+$413. $C_{28}H_{32}N_2O$ requires 412.<br>0.93–1.11(4H, m), 1.24–1.28(1H, m), 1.42–1.48 (2H, m), 1.73–1.77(2H, m), 1.88–1.91(2H, m), 2.70(2H, t, J=8Hz), 3.70(2H, s), 3.74(1H, m), 3.89(4H, s), 5.17(1H, d, J=8Hz), 7.17(4H, s), 7.36(1H, dd, J=8, 2Hz), 7.47–7.50(2H, m), 7.70 (1H, s) and 7.80–7.90(3H, m). |

-continued

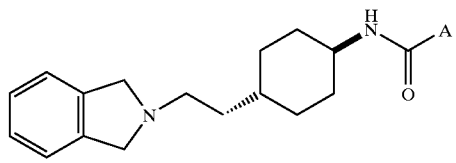

| Example | A | Characterising Data<br>Mass spectrum (API⁺)<br>¹HNMR δ(CDCl₃ or d₆-DMSO) |
|---|---|---|
| 6 | (3-ethylindole) | MH⁺402. $C_{26}H_{31}N_3O$ requires 401.<br>0.86–0.94(2H, m), 1.03–1.07(2H, m), 1.24–1.28 (1H, m), 1.40–1.48(2H, m), 1.70–1.74(2H, m), 1.84–1.88(2H, m), 2.67(2H, t, J=8Hz), 3.70(2H, s), 3.74(1H, m), 3.86(4H, s), 5.46(1H, d, J=8 Hz), 7.12–7.14(1H, m), 7.16(4H, s), 7.23–7.26(2H, m), 7.39(1H, d, J=8Hz), 7.54(1H, d, J=8Hz) and 8.21(1H, s). |
| 7 | (4-ethylquinoline) | MH⁺414. $C_{27}H_{31}N_3O$ requires 413.<br>0.85–0.94(2H, m), 0.94–1.10(2H, m), 1.20–1.30 (1H, m), 1.35–1.50(2H, m), 1.68–1.80(2H, m), 1.82–1.90(2H, m), 2.68(2H, t, J=8Hz), 3.74(1H, m), 3.88(4H, s), 3.97(2H, s), 5.12(1H, br s), 7.14 (4H, s), 7.33(1H, d, J=3Hz), 7.60(1H, m), 7.75 (1H, m), 7.97(1H, d, J=7Hz), 8.14(1H, d, J=7 Hz), 8.88(1H, d, J=3Hz). |

The Following Compounds Were Prepared According to the Procedures of Descriptions 3 and 4 and Example 1

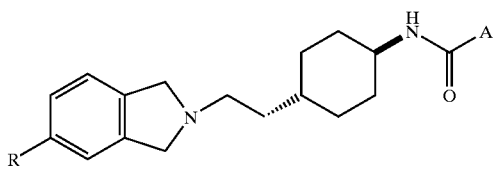

| Example | R | A | Characterising Data<br>Mass spectrum (API⁺) |
|---|---|---|---|
| 8 | NC— | 3-indoyl(7-aza) | Found 414. $C_{25}H_{27}N_5O$ requires 413. |
| 9 | NC— | —CH=CHPh(4-F) | Found 418. $C_{26}H_{28}FN_3O$ requires 417. |
| 10 | NC— | —CH=CHPh(3-OMe) | Found 430. $C_{32}H_{31}N_3O_2$ requires 429. |
| 11 | NC— | —CH=CHPh(2-OMe) | Found 430. $C_{27}H_{31}N_3O_2$ requires 429. |
| 12 | NC— | —CH=CHPh(2-CN) | Found 425. $C_{27}H_{28}N_4O$ requires 424. |
| 13 | NC— | —CH=CH(3-thienyl) | Found 406. $C_{24}H_{27}N_3OS$ requires 405. |
| 14 | NC— | —CH=CH(2-thienyl) | Found 406. $C_{24}H_{27}N_3OS$ requires 405. |
| 15 | MeSO₂O— | —CH=CHPh(4-F) | Found 487. $C_{26}H_{31}FN_2O_4S$ requires 486. |
| 16 | MeSO₂O— | 5-quinolinyl(2-Me) | Found 508. $C_{28}H_{33}N_3O_4S$ requires 507. |
| 17 | MeSO₂O— | —Ph(3-(1-pyrazolyl)) | Found 509. $C_{27}H_{32}N_4O_4S$ requires 508. |

What is claimed is:

1. A compound of formula (I):

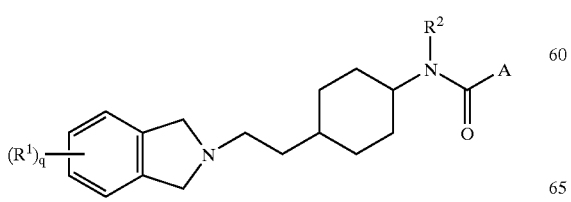

Formula (I)

wherein:

R¹ represents a substituent selected from: a hydrogen atom, a halogen atom, a cyano, trifluoromethyl, trifluoromethoxy, pentafluoroethyl, methyl or methylsulfonyloxy group;

R² represents a hydrogen atom or a $C_{1-4}$ alkyl group;

q is 1 or 2;

A represents a group of the formula (a), (b), (c) or (d):

—Ar  (a)

—Ar¹—Y—Ar²  (b)

19

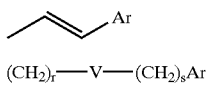

(c)

(CH₂)ᵣ—V—(CH₂)ₛAr    (d)

wherein
Ar represents an optionally substituted phenyl ring or an optionally substituted 5- or 6-membered aromatic heterocyclic ring; or an optionally substituted bicyclic aromatic or heteroaromatic ring systems;
Ar¹ and Ar² each independently represent an optionally substituted phenyl ring or an optionally substituted 5- or 6-membered aromatic heterocyclic ring, and wherein the rings Ar, Ar¹ and Ar² may each independently be optionally substituted by one or more of the substituents selected from a hydrogen or halogen atom, or a hydroxy, oxo, cyano, nitro, trifluoromethyl, $C_{1-4}$alkyl, $C_{1-4}$alkoxy, $C_{1-4}$alkylenedioxy, $C_{1-4}$alkanoyl, $C_{1-4}$alkylsulfonyl, $C_{1-4}$alkylsulfinyl, $C_{1-4}$alkylthio, $R^7SO_2N(R^8)$—, $R^7R^8NSO_2$—, $R^7R^8N$—, $R^7R^8NCO$—, or $R^7CON(R^8)$— group wherein each of $R^7$ and $R^8$ independently represents a hydrogen atom or a $C_{1-4}$ alkyl group, or $R^7R^8$ together form a $C_{3-6}$ alkylene chain; and wherein in the rings Ar and Ar² any substituents positioned ortho to one another may optionally be linked to form a 5- or 6-membered ring; and
Y represents a bond, —NHCO—, —CONH—, —CH₂—, or —(CH₂)ₘY¹(CH₂)ₙ—, wherein Y¹ represents O, S, SO₂, or CO and m and n each represent zero or 1 such that the sum of m+n is zero or 1; providing that when A represents a group of formula (a), any substituent present in Ar ortho to the carboxamide moiety is necessarily a hydrogen or a methoxy group;
r and s independently represent an integer from zero to 3 such that the sum of r and s is equal to an integer from 1 to 4;
V represents a bond, O or S;
or a physiologically acceptable salt thereof.

2. A compound or physiologically acceptable salt as claimed in claim 1 wherein q represents 1.

3. A compound or physiologically acceptable salt as claimed in claim 1 which is in the trans configuration with respect to the cyclohexyl ring.

4. A compound which is:
trans-2-(2-(1-(4-(4-quinolinyl)carboxamido)cyclohexyl) ethyl)-2,3-dihydro-1H-isoindole;
trans-(E)-2-(2-(1-(4-(3-(3-methanesulfonyl) phenylpropenoyl)amino)cyclohexyl)ethyl)-2,3-dihydro-1H-isoindole;
trans-(E)-2-(2-(1-(4-(3-(4-fluoro)phenylpropenoyl)amino) cyclohexyl)ethyl)-2,3-dihydro-1H-isoindole;
trans-2-(2-(1-(4-(3-(3-pyridyl)benzamido))cyclohexyl) ethyl)-2,3-dihydro-1H-isoindole;
trans-2-(2-(1-(4-(2-naphthyl)acetamido))cyclohexyl)ethyl)-2,3-dihydro-1H-isoindole;
trans-2-(2-(1-(4-(3-indolyl)acetamido))cyclohexyl)ethyl)-2,3-dihydro-1H-isoindole;
trans-2-(2-(1-(4-(4-quinolinyl)acetamido))cyclohexyl) ethyl)-2,3-dihydro-1H-isoindole;
trans-5-Cyano-2-(2-(1-(4-(3-pyrrolo[2,3-b]pyridyl) carboxamido)cyclohexyl)ethyl)-2,3-dihydro-1H-isoindole;
trans-(E)-5-Cyano-2-(2-(1-(4-(3-(4-fluoro) phenylpropenoyl)amino)cyclohexyl)ethyl)-2,3-dihydro-1H-isoindole;

20 trans-(E)-5-Cyano-2-(2-(1-(4-(3-(3-methoxy) phenylpropenoyl)amino)cyclohexyl)ethyl)-2,3-dihydro-1H-isoindole;
trans-(E)-5-Cyano-2-(2-(1-(4-(3-(2-methoxy) phenylpropenoyl)amino)cyclohexyl)ethyl)-2,3-dihydro-1H-isoindole;
trans-(E)-5-Cyano-2-(2-(1-(4-(3-(2-cyano) phenylpropenoyl)amino)cyclohexyl)ethyl)-2,3-dihydro-1H-isoindole;
trans-(E)-5-Cyano-2-(2-(1-(4-(3-(3-thiophenyl)propenoyl) amino)cyclohexyl)ethyl)-2,3-dihydro-1H-isoindole;
trans-(E)-5-Cyano-2-(2-(1-(4-(3-(2-thiophenyl)propenoyl) amino)cyclohexyl)ethyl)-2,3-dihydro-1H-isoindole;
trans-(E)-5-Methanesulfonyloxy-2-(2-(1-(4-(3-(4-fluoro) phenylpropenoyl)amino)cyclohexyl)ethyl)-2,3-dihydro-1H-isoindole;
trans-5-Methanesulfonyloxy-2-(2-(1-(4-(5-(2-methyl) quinolinyl)carboxamido)cyclohexyl)ethyl)-2,3-dihydro-1H-isoindole;
trans-5-Methanesulfonyloxy-2-(2-(1-(4-(3-(3-(1-pyrazolyl) benzamido)))cyclohexyl)ethyl)-2,3-dihydro-1H-isoindole;
or a salt thereof.

5. A process for preparing a compound or salt of formula (I) as claimed in claim 1 which process comprises:
(a) reacting a compound of formula(II):

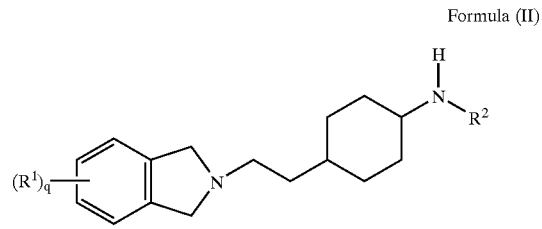

Formula (II)

wherein $R^1$, $R^2$, and q are as defined in claim 1, with a compound of formula (III):

A—COX    Formula (III)

wherein A is as defined in claim 1, and X is a halogen atom or the residue of an activated ester; or
(b) reacting a compound of formula (II) with a compound A—Br, or A—I, or A—OSO₂CF₃ in the presence of carbon monoxide and a catalyst; or
(c) preparing a compound of formula (I) where A represents a group of the formula (b) and Y is a bond, by reacting a compound of formula (VI):

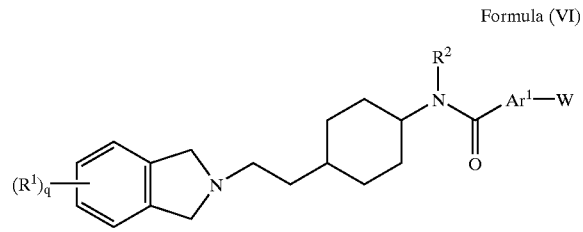

Formula (VI)

wherein $R^1$, $R^2$, q, $Ar^1$ are as defined in claim 1 and W is a halogen atom or a trifluoromethylsulfonyloxy group, or W is a group M selected from a boron derivative or a metal function,
with a compound Ar²—W¹, wherein W¹ is a halogen atom or a trifluoromethylsulfonyloxy group when W is a group M, or $W^1$ is a group M selected from a boron derivative or a metal function when W is a halogen atom or a trifluoromethylsulfonyloxy group; or (d) interconverting one compound of formula (I) to a different compound of formula (I) by (i) alkylation of a compound (I) wherein $R^2$ represents hydrogen; (ii) conversion of one $R^1$ from alkoxy to hydroxy; or (iii) conversion of $R^1$ from hydroxy to sulfonyloxy; (iv) conversion of a compound wherein Y represents S to a compound wherein Y is $SO_2$; or (v) conversion of Y from CO to $CH_2$; or (e) separating cis- and trans-isomers of compounds of formula (I) by conventional methods;

and optionally thereafter forming a physiologically acceptable salt of formula (I).

6. A pharmaceutical composition comprising a compound of formula (I) as claimed in claim 1 or a physiologically acceptable salt thereof and a physiologically acceptable carrier therefor.

* * * * *